United States Patent
Unser

[11] Patent Number: 5,897,853
[45] Date of Patent: Apr. 27, 1999

[54] FINGERNAIL CONDITIONING SYSTEM

[76] Inventor: Lisa Unser, 1909 NE. 20$^{th}$ St., Cape Coral, Fla. 33909-4719

[21] Appl. No.: 08/953,912

[22] Filed: Oct. 20, 1997

[51] Int. Cl.$^6$ .............................. A61K 6/00; A61K 7/00; A61K 7/04

[52] U.S. Cl. ........................... 424/61; 424/401; 424/602; 424/682

[58] Field of Search .......................... 424/401, 61, 602, 424/682; 426/72

[56] References Cited

U.S. PATENT DOCUMENTS

| | | | |
|---|---|---|---|
| 4,626,428 | 12/1986 | Weisberg et al. | 424/61 |
| 4,897,261 | 1/1990 | Yamazaki et al. | 424/61 |
| 4,919,920 | 4/1990 | Devos | 424/61 |
| 5,415,855 | 5/1995 | Critchley et al. | 424/61 |
| 5,445,822 | 8/1995 | Bracco | 424/401 |
| 5,700,455 | 12/1997 | Hinterwaldner et al. | 424/70.14 |

*Primary Examiner*—Thurman K. Page
*Assistant Examiner*—Sharon Howard
*Attorney, Agent, or Firm*—William E. Noonan

[57] ABSTRACT

A fingernail conditioning system and a method for conditioning fingernails are disclosed. The conditioning system includes a power comprising minerals, vitamins and amino acids, an oil comprising minerals, vitamins and an aromatic scent, and an adhesive. The fingernail is first cleaned. Adhesive and powder are applied and the nail is buffed. Adhesive is then applied to the buffed nail and permitted to dry. Oil is the applied to the nail and the nail is buffed until it is smooth.

9 Claims, 2 Drawing Sheets

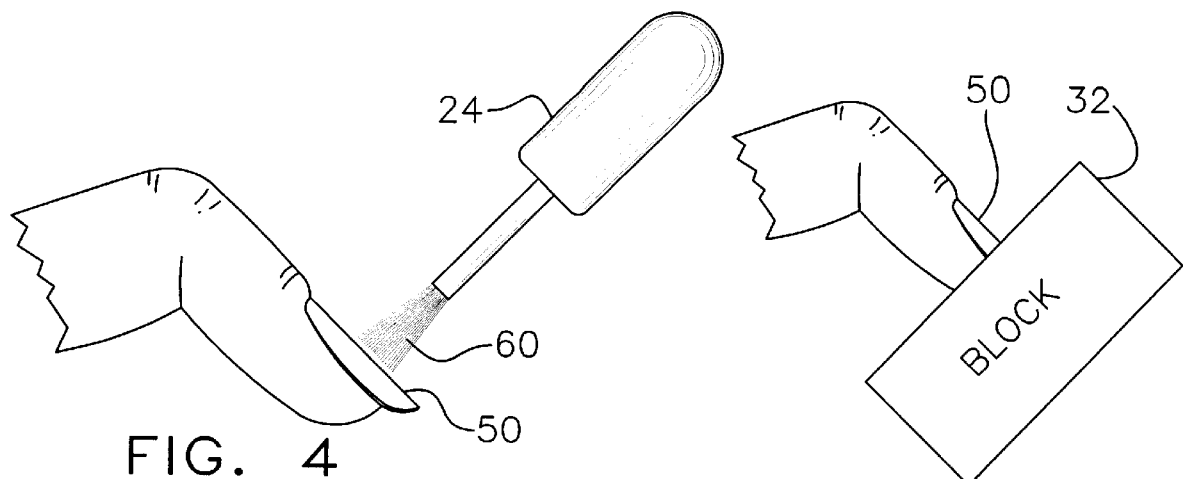
FIG. 4
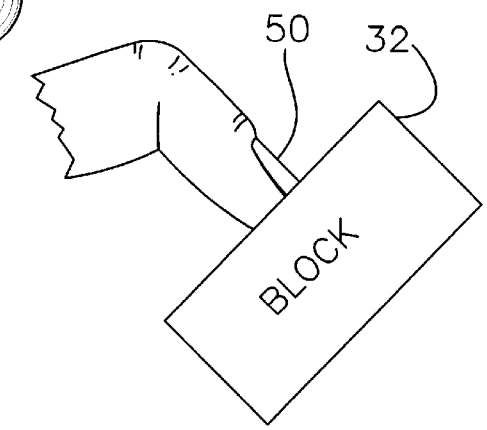
FIG. 7
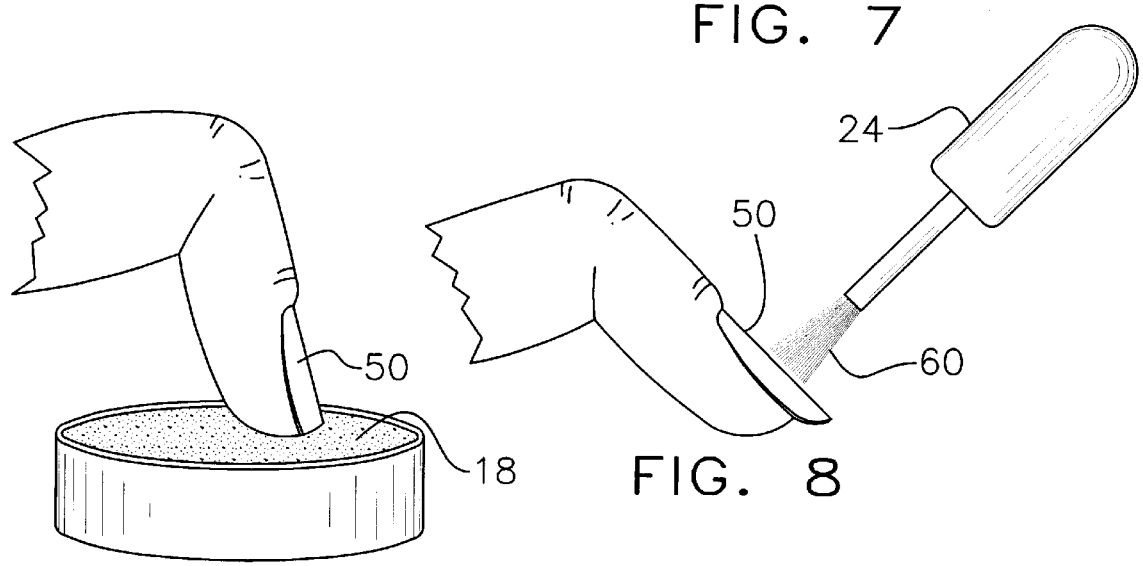
FIG. 5
FIG. 8
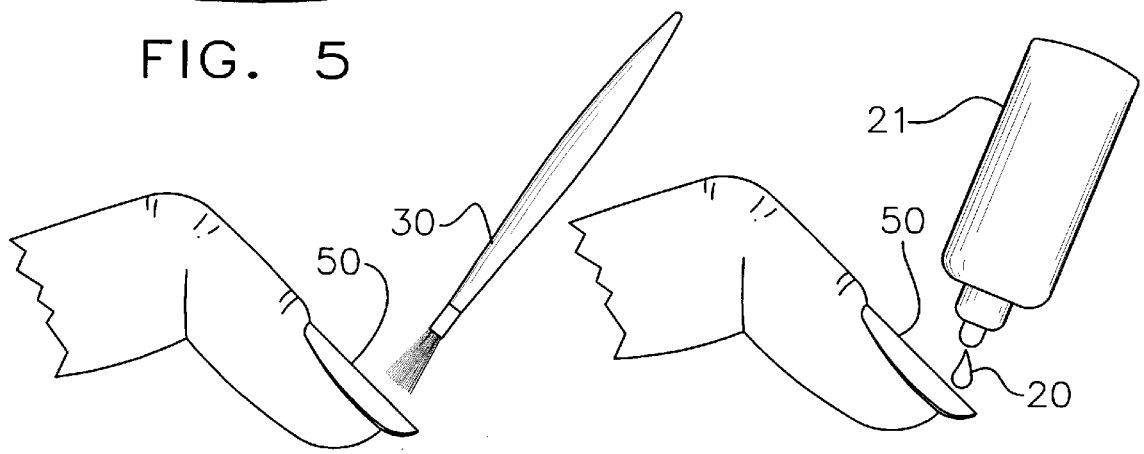
FIG. 6
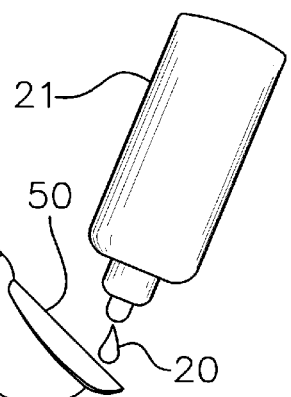
FIG. 9

FINGERNAIL CONDITIONING SYSTEM

FIELD OF THE INVENTION

This invention relates to a fingernail conditioning system and, more particularly, to a product and technique for strengthening, conditioning and protecting fingernails.

BACKGROUND OF THE INVENTION

Fingernails frequently break, split, crack and are otherwise damaged. Fingernail deterioration is accelerated by the harsh chemicals typically contained in most fingernail polishes. Damaged nails can be painful, unsightly and unhealthy. In order to cosmetically remedy this problem many women have artificial fingernails applied to their natural nails. This is not a totally satisfactory solution, however. Artificial nails typically must be applied using harsh and malodorous chemicals. The underlying nail may have to be etched with an acid primer, which damages the natural nail even further. Moreover, artificial nail applications may be painful and many persons are allergic to the chemicals that are used. This procedure is usually fairly costly and, in many cases, the artificial nail does not present a perfectly natural appearance. When such nails are eventually removed, the underlying natural nails usually exhibits considerable damage and remain unattractive for a significant period of time.

SUMMARY OF INVENTION

It is therefore an object of this invention to provide a fingernail conditioning system, which effectively strengthens and protects the wearer's natural fingernails.

It is a further object of this invention to provide a fingernail conditioning system that helps to quickly and effectively repair previously damaged nails.

It is a further object of this invention to provide a fingernail conditioning system that does not utilize harsh chemicals and thereby eliminates the offensive odors, allergic reactions and fingernail damage often caused by the use of such chemicals on the nails.

It is a further object of this invention to provide a fingernail conditioning system that leaves the fingernails in a healthy and rejuvenated condition.

It is a further object of this invention to provide fingernail conditioning system that stimulates tissue growth and development.

It is a further object of this invention to provide fingernail conditioning system, which presents the nails with an attractive appearance and a pleasant aroma.

It is a further object of this invention to provide fingernail conditioning system, which conditions the fingernails naturally and eliminates virtually all of the problems associated with the use and application of artificial fingernails and conventional nail conditioning products.

This invention features a fingernail conditioning system that employs powder, oil and glue components. The powder comprises calcium, magnesium, iron, vitamins C and E, amino acids and whey. The oil includes a variety of vitamins, including vitamins A, B1, B2, B3, B6, B12, C, D3 and E. The majority of the oil comprises mineral oil. A scent such as jasmine may also be included in the oil. The glue includes cyanoacrylate or an equivalent component. This glue should bond in seconds, be lightweight and clear, and contain no offensive odors.

This invention also features a method for applying the above-described conditioning system to a human fingernail. Initially, an unpolished the nail may be sprayed with alcohol and wiped dry. The glue is then applied to the nail, by means of a conventional fingernail applicator brush. The powder is then applied to the nail before the glue has dried. Excess powder is brushed from the nail by a conventional soft fingernail brush. The nail may then be buffed and the preceding steps repeated one or more times. After these steps, the nail is brushed again to remove any excess powder remaining on the nail. An additional layer of glue is applied to the nail and allowed to dry. After the nail has dried, oil is applied to the nail and the nail is buffed, such as by a standard buffing block, until the nail is in a generally smooth condition. Finally, the nail may be washed and dried and fingernail polish may be applied in a conventional manner.

BRIEF DESCRIPTION OF THE DRAWINGS

Other objects, features and advantages will occur from the following description of preferred embodiments and the accompanying drawings, in which:

FIG. 4 is a perspective view of the fingernail with glue being applied thereto by a brush;

FIG. 5 is a perspective view of the fingernail being dipped into the powder while the glue is in a wet condition;

FIG. 6 is a perspective view of the fingernail being brushed free of excess powder;

FIG. 7 is a perspective view of the fingernail being buffed;

FIG. 8 is a perspective view of the final coat of glue being applied to the fingernail; and FIG. 9 is a perspective view of the oil being applied to the fingernail.

DETAILED DESCRIPTION OF PREFERRED EMBODIMENTS

Figure 1:
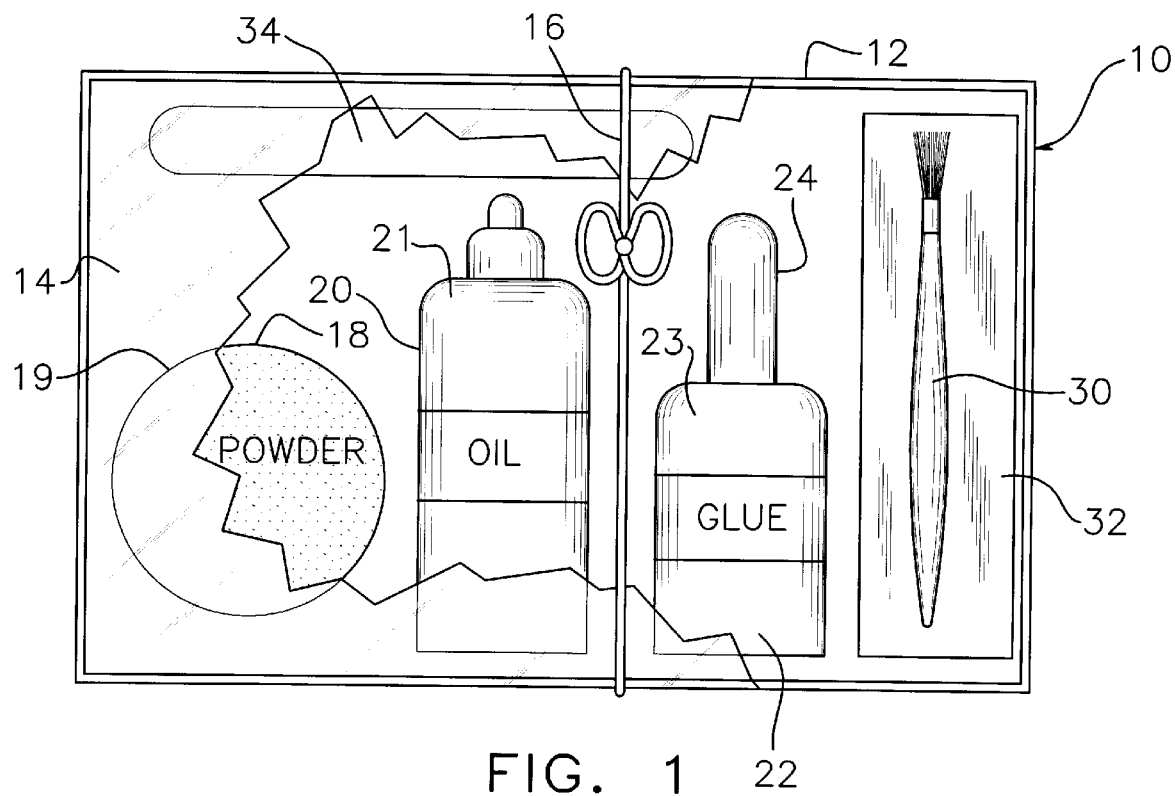
FIG. 1 is an plan view of a kit that includes the fingernail conditioning system of this invention.

There is shown in FIG. 1 a nail conditioning system 10, which is packaged in a standard container 12. It should be understood that virtually all sizes and shapes of containers may be utilized. In the embodiment disclosed herein, a rectangular container is employed and a transparent cover or lid 14 is secured to the box by an elastic cord 16.

The nail conditioning system features three primary components: a power 18, an oil 20 and an adhesive 22. Powder 18 is typically disposed in a jar, dish or tub 19. Oil 20 and adhesive 22 are contained in respective bottles. Various sizes and shapes of containers may be utilized. Preferably, oil 20 is accommodated in a dispenser-type bottle 21, which may be squeezed in a standard manner to dispense one or more drops of oil. Adhesive 22 is typically contained in a bottle 23 wherein the cap 24 carries an applicator brush that is stored inside of the bottle. When the cap is opened, the brush may be pulled out and used to apply the adhesive in a manner described more fully below. In FIG. 1, the brush is hidden from view because cap 24 is closed on bottle 23.

Powder 18 comprises various proteins, minerals, vitamins and amino acids within a gelatin binder. Entirely natural ingredients are utilized. These constituents are lightweight and serve as an organic tissue builder. The following is a list of the preferred ingredients of the powder and their respective concentrations.

| Calcium | 25% |
|---|---|
| Magnesium | 20% |
| Iron | 10% |
| Vitamin E | 15% |
| Vitamin C | 5% |
| Amino Acids | 20% |
| Whey | 5% |

At a minimum the powder should include at least one of calcium, magnesium and iron, at least one of Vitamins C and E and at least one amino acid. The above concentrations may be varied somewhat within the scope of this invention. The powder is prepared and its constituents are mixed using various techniques, which will be understood to those skilled in the art.

Oil 20 includes vitamins, minerals and an additive that provides an aromatic scent. Typically, a mineral oil base is employed. Jasmine is a preferred scent. The following is a list of the typical constituents of the oil and their respective concentrations.

| Mineral Oil | 80% |
|---|---|
| Jasmine | 10% |
| Vitamin A | 1% |
| Vitamin B1 | 1% |
| Vitamin B2 | 1% |
| Vitamin B3 | 1% |
| Vitamin B6 | 1% |
| Vitamin B12 | 1% |
| Vitamin C | 1.5% |
| Vitamin D3 | 1% |
| Vitamin E | 1.5% |

Once again, the above concentrations may be modified somewhat within the scope of this invention. The formula described above yields the following benefits when the oil is applied to the fingernails in accordance with this invention. Vitamin A promotes healthy skin; Vitamin B energizes the nails; Vitamins C and D promote tissue growth and development; and Vitamin E rejuvenates the skin. A scent such as jasmine helps to relax the wearer by emitting a fresh and light, aesthetically pleasing aroma.

Adhesive 22 preferable comprises a glue, such as cyanoacrylate or a substantially similar adhesive compound. The glue that is used should cause minimal dehydration to the fingernails and should not emit harsh odors.

Kit 10 also includes various accessories such as a soft brush 30, a buffing block 32 and a nail file 34. These components are likewise contained in box 12 and may be used during the fingernail conditioning process described below. Healthy, attractive and damage resistant fingernails are achieved when the system of this invention is applied to the nails. This process is depicted in FIGS. 2–9.

Figure 2:
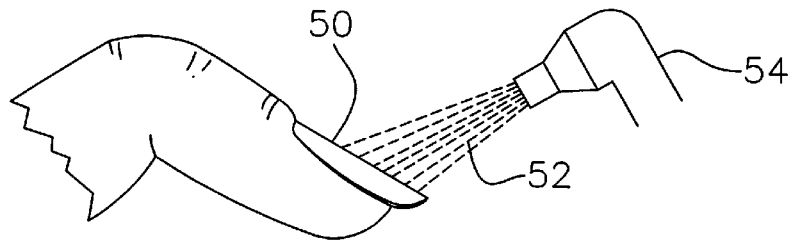
FIG. 2 is a perspective view of a fingernail being prepared for application of the conditioning system of this invention by having alcohol sprayed thereon.
Figure 3:
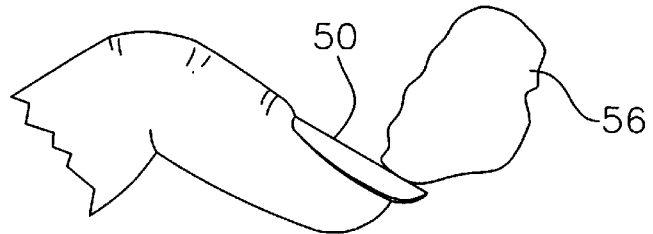
FIG. 3 is a perspective view of the fingernail being wiped dry of the alcohol.

As shown in FIG. 2, an individual fingernail 50 is initially prepared for conditioning by spraying or otherwise applying alcohol 52 to the nail. Alcohol is applied by a conventional spray bottle 54, the top of which is shown in FIG. 2. Alcohol 52 is sprayed onto the unpolished nail. The nail is then dried by a cloth 56 in the manner shown in FIG. 3. As a result, fingernail 50 is cleaned of dirt and other impurities.

As shown in FIG. 4, fingernail 50 is extended outwardly and somewhat downwardly so that glue can be applied conveniently to the nail. In particular, bottle 23, shown in FIG. 1, is accessed by the wearer, nail technician or other person applying the system, and cap 24 is removed from the bottle. As illustrated in FIG. 4, a brush 60 depends from cap 24. This brush carries glue from the bottle and this glue is applied to nail 50 by brushing the nail in a conventional manner. Before the glue dries, fingernail 50 is dipped into powder 18 in the manner depicted in FIG. 5. The powder and its constituent vitamins and minerals are thereby adhered to the fingernail. Excess powder on nail 50 is brushed off of the nail by soft brush 30, FIG. 6. The fingernail is then buffed to the pink of the nail by block 32, in the manner shown in FIG. 7. The nail should be buffed in this manner until the nail is essentially transparent. Brush 30 is then used to remove any excess dust from the nail.

The above process is typically repeated two or more times. This gradually strengthens and conditions the nail. Vitamins, minerals and proteins (amino acids) are absorbed into the nail. As shown in FIG. 8, a final coat of glue is applied by brush 60 to nail 50. This coat is permitted to dry. As shown in FIG. 9, oil bottle 21 is then inverted and a drop of oil 20 is dispensed onto fingernail 50. The oil is buffed into the nail using block 32, FIGS. 1 and 7. The vitamins, minerals and aromatic scent contained in the oil are imparted to nail 50. This conditions, strengthens and protects the nail and results in the previously described benefits. Subsequently, fingernail 50 is washed, dried and polished with a conventional fingernail polish, which is selected to provide a desired color or texture.

In order to remove the polish, a non-acetone polish remover is applied to the nail. The components of the conditioning system itself may be removed from the nail by soaking the fingernail for approximately 15 minutes in an acetone-based polish remover or in pure acetone. An orange wood stick or a similar device may be employed to urge the conditioning components off of the nail while it is soaking.

It should be noted that the above-described fingernail conditioning system may be used by both men and women. Typically, when women utilize the product, the conditioned nails are polished. Artificial fingernail tips may also be applied to the conditioned nail. Alternatively, when men utilize the product, the conditioned fingernails normally remain unpolished. In either case, the vitamins and other nutrients utilized in the conditioning system are absorbed into the nail and provide for healthy, attractive and damage-resistant fingernails. The nails resist splitting, softening and breaking and the problems that typically accompany the use of artificial nails are greatly reduced. The application of the conditioning system does not produce harsh chemical odors and does not cause the wearer an allergic reaction.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. A fingernail conditioning system comprising:
   an adhesive that is applied to a fingernail;
   a powder that is adhered to the fingernail by said adhesive, said powder including each of at least one amino acid, at least one of the group constituting vitamins C and E and at least one of the group constituting calcium, magnesium and iron, said powder including approximately 25% calcium, 20% magnesium, 10% iron, 15% vitamin E, 5% vitamin C, 20% amino acid and 5% whey; and
   an oil that is applied to the fingernail over said powder and said adhesive and absorbed into the fingernail, said oil including each of at least one mineral, at least one vitamin from the group constituting vitamins A, B1, B2, B3, B6, B12, C, D3 and E and an aromatic scent.

2. The system of claim 1 in which said powder includes whey.

3. The system of claim 1 in which said powder includes calcium, magnesium, iron, vitamins C, E, amino acid and whey.

4. The system of claim 1 in which said oil constitutes 80% mineral oil.

5. The system of claim 1 in which said oil comprises an aromatic scent having a concentration of 10%.

6. The system of claim 1 in which said oil constitutes vitamins A, B1, B2, B3, B6 and B12 and in respective concentrations of 1%, vitamin C in a concentration of 1.5% and vitamin E in a concentration of 1.5%.

7. The system of claim 1 in which said adhesive comprises cyanoacrylic glue.

8. A fingernail conditioning system comprising:

an adhesive that is applied to a fingernail;

a powder that is adhered to the fingernail by said adhesive, said powder including each of at least one amino acid, at least one of the group constituting vitamins C and E and at least one of the group constituting calcium, magnesium and iron; and an oil that is applied to the fingernail over said powder and said adhesive and absorbed into the fingernail, said oil including each of at least one mineral, at least one vitamin from the group constituting vitamins A, B1, B2, B3, B6, B12, C, D3 and E and an aromatic scent, said oil constituting 80% mineral oil.

9. A fingernail conditioning system comprising:

an adhesive that is applied to a fingernail;

a powder that is adhered to the fingernail by said adhesive, said powder including each of at least one amino acid, at least one of the group constituting vitamins C and E and at least one of the group constituting calcium, magnesium and iron; and an oil that is applied to the fingernail over said powder and said adhesive and absorbed into the fingernail, said oil including each of at least one mineral, at least one vitamin from the group constituting vitamins A, B1, B2, B3, B6, B12, C, D3 and E and an aromatic scent, said oil constituting vitamins A, B1, B2, B3, B6 and B12 in respective concentrations of 1%, vitamin C in a concentration of 1.5% and vitamin E in a concentration of 1.5%.

* * * * *